United States Patent [19]
Ueda et al.

[11] Patent Number: 5,633,143
[45] Date of Patent: May 27, 1997

[54] METHOD FOR THE QUANTITATIVE DETERMINATION OF D-3-HYDROXYBUTYRIC ACID AND ACETOACETIC ACID, AND ANALYTICAL REAGENT THEREFOR

[75] Inventors: Shigeru Ueda; Hideo Misaki; Shigeru Ikuta, all of Tagata-gun; Mamoru Takahashi, Sunto-gun, all of Japan

[73] Assignee: Asahi Kasei Kogyo Kabushiki Kaisha, Osaka, Japan

[21] Appl. No.: 244,450

[22] PCT Filed: Dec. 12, 1991

[86] PCT No.: PCT/JP91/01706

§ 371 Date: May 26, 1994

§ 102(e) Date: May 26, 1994

[87] PCT Pub. No.: WO93/12254

PCT Pub. Date: Jun. 24, 1993

[51] Int. Cl.$^6$ .................. C12Q 1/32; C12Q 1/52; G01N 33/53; G01N 31/00
[52] U.S. Cl. .................. 435/26; 435/25; 435/16; 435/15; 435/4; 435/966; 435/973; 436/14; 436/2; 436/63; 436/71; 436/74; 536/1.11
[58] Field of Search .................. 435/26, 25, 4, 435/16, 15, 966, 973; 436/11, 14, 2, 63, 71, 74; 536/1.11

[56] References Cited

U.S. PATENT DOCUMENTS

| | | | |
|---|---|---|---|
| 4,120,755 | 10/1978 | Pierre et al. | 435/26 |
| 5,032,506 | 7/1991 | Palmer et al. | 435/26 |
| 5,037,738 | 8/1991 | Lamos et al. | 435/25 |
| 5,190,863 | 3/1993 | Magers | 435/25 |
| 5,266,463 | 11/1993 | Takahashi et al. | 435/26 |
| 5,286,627 | 2/1994 | Ueda et al. | 435/25 |

OTHER PUBLICATIONS

Saito et al, Chem. Pharm. Bull. vol. 38(6), pp. 1627–1629, (1990).
Lippolis et al, Archives of Biochem & Biophysics, vol. 260, No. 1, pp. 94–101, Jan. 1988.
Clinical Chimica Acta, 134, 327–336 (1983).
Extra–Edition of Japanese Journal of Clinical Medicine, 47, 482–485 (1989).
Method of Enzymatic Analysis, 1836–1843 (1974).
Diabetes Care, 7, 481–485 (1984).

*Primary Examiner*—John Kight
*Assistant Examiner*—Louise N. Leary
*Attorney, Agent, or Firm*—Pennie & Edmonds

[57] ABSTRACT

Disclosed is a method for the quantitative determination of D-3-hydroxybutyric acid and acetoacetic acid, which comprises reacting a biological sample containing D-3-hydroxybutyric acid and acetoacetic acid, with a reagent comprising: (1) a D-3-hydroxybutyrate dehydrogenase, (2)

$A_1$ and (3) $B_1$, the components (1), (2) and (3) participating in the following cycling reaction:

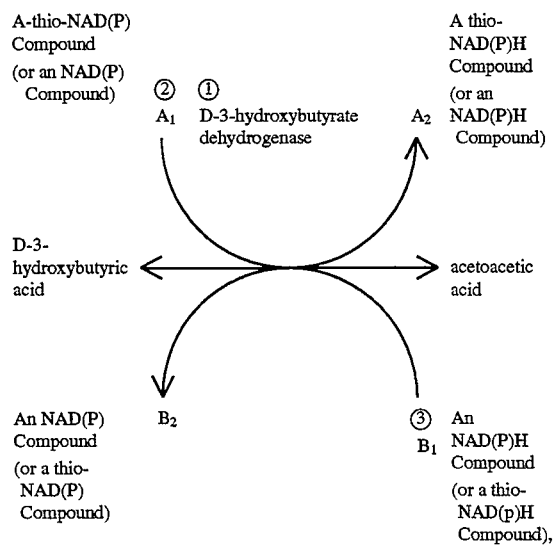

thereby effecting the enzymatic cycling reaction, and measuring a change in the amount of $A_2$ formed or the amount of $B_1$ consumed. Also disclosed is an analytical reagent comprising the components (1), (2) and (3) for use in the above method. The method and the analytical reagent ensure rapidness and accuracy in the determination of D-3-hydroxybutyric acid and acetoacetic acid, even with the use of a small quantity of a biological sample, so that they are very useful in application fields, such as clinical diagnosis and food testing.

26 Claims, 4 Drawing Sheets

D-3-Hydroxybutyric Acid Concentration (μM)

Acetoacetic Acid Concentration (μM)

Acetoacetic Acid Concentration (μM)

METHOD FOR THE QUANTITATIVE DETERMINATION OF D-3-HYDROXYBUTYRIC ACID AND ACETOACETIC ACID, AND ANALYTICAL REAGENT THEREFOR

TECHNICAL FIELD

The present invention relates to a method for the quantitative determination of D-3-hydroxybutyric acid and acetoacetic acid utilizing an enzymatic cycling reaction. The present invention also relates to a novel analytical reagent for use in the above-mentioned quantitative determination.

BACKGROUND ART

In clinical examination, it is important to determine ketone bodies, such as D-3-hydroxybutyric acid and acetoacetic acid, as criteria for detecting metabolic failure. In addition to the above-mentioned two types of ketone bodies, acetone can also be mentioned as a ketone body. However, acetone is volatile and unstable. In addition, the concentration of acetone in blood is considerably low as compared to the concentrations of D-3-hydroxybutyric acid and acetoacetic acid. This means that a metabolic failure can be successfully detected even by determining only D-3-hydroxybutyric acid and acetoacetic acid among ketone bodies.

Examples of conventional methods for the determination of ketone bodies include the diazonium method in which acetoacetic acid is reacted with a diazonium salt to thereby produce a hydrazo compound or an azo compound, and the absorbance of the produced hydrazo or azo compound is measured; the nitroprusside method in which acetoacetic acid and acetone are reacted with a nitroprusside reagent to thereby convert acetoacetic acid and acetone to respective colorimetrically-detectable forms; the gas chromatographic method in which D-3-hydroxybutyric acid and acetoacetic acid are converted to acetone and all of the ketone bodies are quantitatively determined in terms of acetone by gas chromatography; and the enzymatic method.

Although the diazonium method exhibits high sensitivity, the method requires deprotenization of a biological sample before conducting the reaction of acetoacetic acid with a diazonium salt. Further, for determining D-3-hydroxybutyric acid by the diazonium method, the following cumbersome operations are required. Acetoacetic acid in a biological sample is determined and then, D-3-hydroxybutyric acid in the sample is converted to acetoacetic acid by D-3-hydroxybutyrate dehydrogenase, followed by measurement of the acetoacetic acid (which is converted from the D-3-hydroxybutyric acid), thus quantitatively determining both of the D-3-hydroxybutyric acid and acetoacetic acid in the sample. Then, the quantity of D-3-hydroxybutyric acid is obtained by subtracting the quantity of acetoacetic acid from the above-mentioned total quantity of D-3-hydroxybutyric acid and acetoacetic acid. However, the conventional methods in which a ketone body is quantitatively determined by reacting the ketone body with a chemical reagent generally has low specificity and, therefore, the determination of a target substance is likely to be influenced by other substances present in a biological sample. For example, in the diazonium method, the determination of acetoacetic acid in a biological sample is likely to be influenced by oxaloacetic acid (Clinica Chemica Acta, vol. 134, p.327–336, 1983). With respect to the nitroprussid method, this method has disadvantages in that not only cannot D-3-hydroxybutyric acid be directly detected as in the case of the diazonium method, but also the method exhibits low sensitivity (detection sensitivity: 500 to 1000 µM) (Extra-edition of Japanese Journal of Clinical Medicine vol, 47, p.484, 1989).

Further, the gas chromatographic method is extremely cumbersome and, therefore, the method is not suitable for use in clinical examination in which a lot of biological samples are to be tested.

With respect to the enzymatic method, there can be mentioned Williamson method (Method of Enzymatic Analysis, Academic Press, New York, p.1836–1843, 1974) in which the enzymatic reaction of D-3-hydroxybutyrate dehydrogenase (EC 1. 1. 1. 30) is utilized. In this method, when acetoacetic acid in a biological sample is to be determined, the reverse enzymatic reaction under the action of D-3-hydroxybutyrate dehydrogenase is utilized in which acetoacetic acid and a reduced form of nicotinamide adenine dinucleotide (NAD) are, respectively, converted to D-3-hydroxybutyric acid and NAD. That is, a decrease in the amount of reduced NAD (which decrease corresponds to the amount of reduced NAD consumed in the above reverse reaction) which decrease is caused for a predetermined period of time is measured. On the other hand, when D-3-hydroxybutyric acid in a biological sample is to be determined, the forward enzymatic reaction under the action of D-3-hydroxybutyrate dehydrogenase is utilized in which D-3-hydroxybutyric acid and NAD are, respectively, converted to acetoacetic acid and reduced NAD. That is, an increase in the amount of reduced NAD (which increase corresponds to the amount of reduced NAD produced in the above forward reaction) which increase is caused for a predetermined period of time is measured. A modification of the Williamson method was also proposed.

As another example of the enzymatic method, there can be mentioned a paper strip testing for the determination of D-3-hydroxybutyric acid. In this method, the forward enzymatic reaction under the action of D-3-hydroxybutyrate dehydrogenase is utilized in which D-3-hydroxybutyric acid and NAD are, respectively, converted to acetoacetic acid and reduced NAD under the action of D-3-hydroxybutyrate dehydrogenase. An increase in the amount of reduced NAD corresponds to the amount of reduced NAD produced in the above forward enzymatic reaction. The amount of the D-3-hydroxybutyric acid can be determined based on the increase in the amount of reduced NAD. The reduced NAD obtained in the above enzymatic reaction is reacted with a tetrazolium salt on a strip paper, and then a formazan dye produced in the amount which is proportional to the increase in the amount of the reduced NAD is determined.

In the above-mentioned enzymatic methods, it is impossible not only to determine both of D-3-hydroxybutyric acid and acetoacetic acid by a single enzymatic reaction, which are clinically important ketone bodies, but also to achieve the determination with high sensitivity.

As still another example of the enzymatic method for the quantitative determination of acetoacetic acid, there can be mentioned a method in which acetoacetic acid is converted to acetyl-CoA by using acetoacetyl-CoA synthetase (EC 6.2.1.16) and 3-ketoacyl-CoA thiolase (EC 2.3.1.16) and then, the acetyl-CoA produced is used for acetylating aniline under the action of arylamine acetylase (EC 2.3.1.5), followed by measurement of a decrease in the amount of acetylated aniline as a decrease in the absorbance at a wavelength of 405 nm (Acta Biochim. Biophys. Acad. Sci. Hung., vol. 7, p.143, 1972). However, this method requires complicated operations. In addition, a highly sensitive method for the determination of ketone bodies cannot be achieved by this method. Therefore, the method has not yet been widely used.

Task to be solved by the invention

As mentioned above, various types of methods for the determination of D-3-hydroxybutyric acid or acetoacetic acid have been proposed. However, as mentioned above, in any of these methods, it is impossible to determine ketone bodies with high sensitivity. In addition, a total quantity of ketone bodies, which are important in clinical examination, cannot be determined by a single enzymatic reaction.

The normal concentrations of ketone bodies in serum or plasma is low. For example, in serum or plasma, the normal concentration of acetoacetic acid is as low as 41 ±1.4 (average value ±standard error) μmol/liter, the normal concentration of D-3-hydroxybutyric acid is 34 ±2.1 μmol/liter, and the total normal concentration of ketone bodies is 74 ±2.4 μmol/liter (Extra-edition of Japanese Journal of Clinical Medicine, vol. 47, p.482, 1989). In the above situation, a highly sensitive method for the determination of D-3-hydroxybutyric acid ad acetoacetic acid has been desired.

Means to Solve the Task

From the above context, the present inventors have made extensive and intensive studies with a view toward solving the above-mentioned problems accompanying the conventional methods for the quantitative determination of a ketone body in biological samples. As a result, they have found that the target chemical substance, i.e., at least one ketone body selected from the group consisting of D-3-hydroxybutyric acid and acetoacetic acid can be quantitatively determined by measuring a change in amount of $A_2$ or $B_1$, which is caused by the cycling reaction represented by the following formula (I):

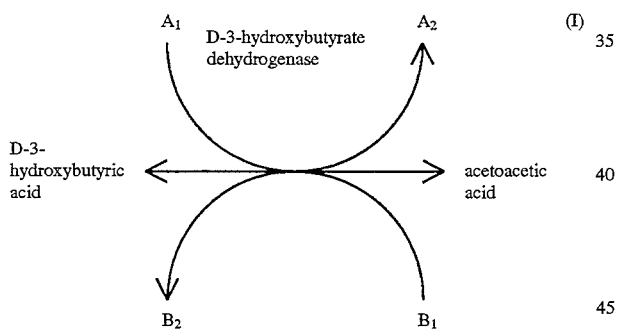

wherein $A_1$ is a thio-NADP compound, a thio-NAD compound, an NADP compound or an NAD-compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized form of $B_1$. The present inventors have also found that the change in the amount of coenzyme $A_2$ or $B_1$ can be easily measured because coenzymes $A_2$ and $B_1$ are different in absorption maximum from each other (a reduced thio-NAD compound and a reduced thio-NADP compound exhibit an absorption maximum at about 400 nm, and a reduced NAD compound and a reduced NADP compound exhibit an absorption maximum at about 340 nm). Thus, a highly sensitive method for the quantitative determination of at least one ketone body selected from the group consisting of D-3-hydroxybutyric acid and acetoacetic acid, which can be simply, efficiently carried out and is less influenced by other substances present in a sample, has been realized. Based upon the above findings, the present invention has been completed.

DISCLOSURE OF THE INVENTION

Figure 1:
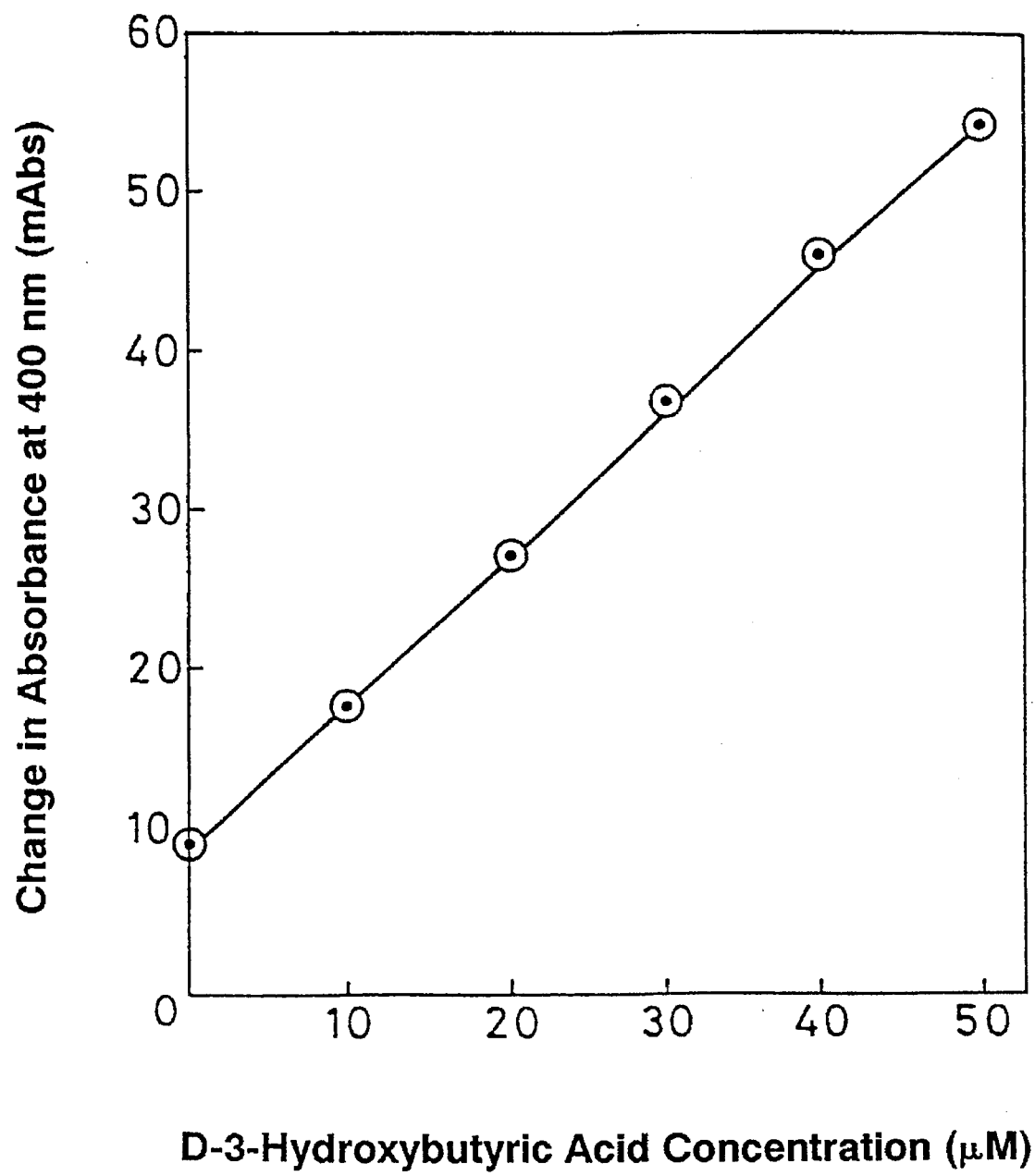
FIG. 1 is a graph showing the results of the rate assay of D-3-hydroxybutyric acid at a wavelength of 400 nm conducted in Example 1.

According to the present invention, there is provided a method for the quantitative determination of at least one ketone body selected from the group consisting of D-3-hydroxybutyric acid and acetoacetic acid, which comprises:

reacting a biological sample containing at least one ketone body selected from the group consisting of D-3-hydroxybutyric acid and acetoacetic acid with a reagent comprising:

(1) a D-3-hydroxybutyrate dehydrogenase which utilizes the following coenzymes (i) and (ii):
(i) a first coenzyme selected from the group consisting of thionicotinamide adenine dinucleotide phosphate or its analog (thio-NADP compound) and thionicotinamide adenine dinucleotide or its analog (thio-NAD compound), and
(ii) a second coenzyme selected from the group consisting of nicotinamide adenine dinucleotide phosphate or its analog (NADP compound) and nicotinamide adenine dinucleotide or its analog (NAD compound), and catalyzes the reversible reaction producing acetoacetic acid from D-3-hydroxybutyric acid as a substrate;

(2) $A_1$ (defined hereinbelow); and
(3) $B_1$ (defined hereinbelow):

the components (1), (2) and (3) participating in the following cycling reaction:

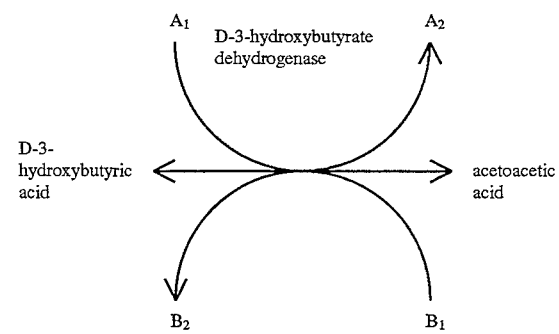

wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized form of $B_1$, thereby effecting the cycling reaction; and measuring a change in the amount of $A_2$ or $B_1$.

In another aspect of the present invention, there is provided a method for the quantitative determination of at least one ketone body selected from the group consisting of D-3-hydroxybutyric acid and acetoacetic acid, which comprises:

reacting a biological sample containing at least one ketone body selected from the group consisting of D-3-hydroxybutyric acid and acetoacetic acid with a reagent comprising:
  (1) a D-3-hydroxybutyrate dehydrogenase as a first dehydrogenase which utilizes the following coenzymes (i) and (ii):
    (i) a first coenzyme selected from the group consisting of thionicotinamide adenine dinucleotide phosphate or its analog (thio-NADP compound) and thionicotinamide adenine dinucleotide or its analog (thio-NAD compound), and
    (ii) a second coenzyme selected from the group consisting of nicotinamide adenine dinucleotide phosphate or its analog (NADP compound) and nicotinamide adenine dinucleotide or its analog (NAD compound),
    and catalyzes the reversible reaction producing acetoacetic acid from D-3-hydroxybutyric acid as a substrate;
  (2) $A_1$ (defined hereinbelow);
  (3) at least one coenzyme selected from, $B_1$ (defined hereinbelow) and $B_2$ (defined hereinbelow); and
  (4) a second dehydrogenase which does not react with D-3-hydroxybutyric acid but acts to promote the reaction for converting $B_2$ to $B_1$ in the following cycling reaction, in combination with a substrate for the second dehydrogenase:
    the components (1), (2), (3) and (4) participating in the following cycling reaction:

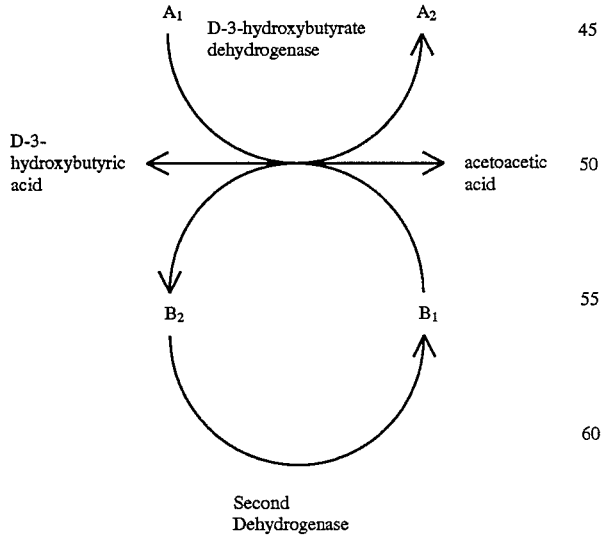

wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; $B_2$ is an oxidized form of $B_1$; and $B_2 \rightarrow B_1$ represents an enzymatic reaction producing $B_1$ from coenzyme $B_2$ under the action of the second dehydrogenase, thereby effecting the cycling reaction; and measuring a change in the amount of $A_2$.

In a further aspect of the present invention, there is provided a method for the quantitative determination of at least one ketone body selected from the group consisting of D-3-hydroxybutyric acid and acetoacetic acid, which comprises:

reacting a biological sample containing at least one ketone body selected from the group consisting of D-3-hydroxybutyric acid and acetoacetic acid with a reagent comprising:
  (1) a D-3-hydroxybutyrate dehydrogenase as a first dehydrogenase which utilizes the following coenzymes (i) and (ii):
    (i) a first coenzyme selected from the group consisting of thionicotinamide adenine dinucleotide phosphate or its analog (thio-NADP compound) and thionicotinamide adenine dinucleotide or its analog (thio-NAD compound), and
    (ii) a second coenzyme selected from the group consisting of nicotinamide adenine dinucleotide phosphate or its analog (NADP compound) and nicotinamide adenine dinucleotide or its analog (NAD compound),
    and catalyzes the reversible reaction producing acetoacetic acid from D-3-hydroxybutyric acid as a substrate;
  (2) at least one coenzyme selected from $A_1$ (defined hereinbelow) and $A_2$ (defined hereinbelow); and
  (3) $B_1$ (defined hereinbelow);
  (5) a third dehydrogenase which does not react with D-3-hydroxybutyric acid but acts to promote the reaction for converting $A_2$ to $A_1$ in the following cycling reaction, in combination with a substrate for the third dehydrogenase:
    the components (1), (2), (3) and (5) participating in the following cycling reaction:

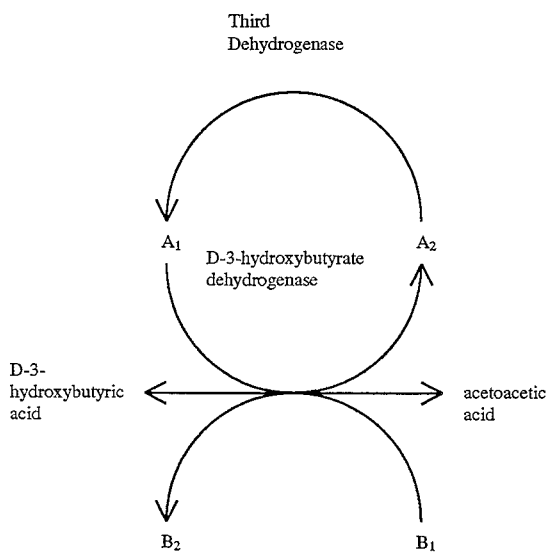

wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; $B_2$ is an oxidized form of $B_1$; and $A_2 \rightarrow A_1$ represents an enzymatic reaction producing $A_1$ from coenzyme $A_2$ under the action of the third dehydrogenase, thereby effecting the cycling reaction; and measuring a change in the amount of $B_1$.

In still a further aspect of the present invention, there is provided an analytical reagent for use in the quantitative determination of at least one ketone body selected from the group consisting of D-3-hydroxybutyric acid and acetoacetic acid, which comprises:

(1) a D-3-hydroxybutyrate dehydrogenase which utilizes the following coenzymes (i) and (ii):

(i) a first coenzyme selected from the group consisting of thionicotinamide adenine dinucleotide phosphate or its analog (thio-NADP compound) and thionicotinamide adenine dinucleotide or its analog (thio-NAD compound), and (ii) a second coenzyme selected from the group consisting of nicotinamide adenine dinucleotide phosphate or its analog (NADP compound) and nicotinamide adenine dinucleotide or its analog (NAD compound), and catalyzes the reversible reaction producing acetoacetic acid from D-3-hydroxybutyric acid as a substrate;

(2) $A_1$ (defined hereinbelow); and (3) $B_1$ (defined hereinbelow), wherein $A_1$ is a thio-NADP compound, a thio-NAD compound, an NADP compound or an NAD compound; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound.

In still a further aspect of the present invention, there is provided an analytical reagent for use in the quantitative determination of at least one ketone body selected from the group consisting of D-3-hydroxybutyric acid and acetoacetic acid, which comprises:

(1) a D-3-hydroxybutyrate dehydrogenase as a first dehydrogenase which utilizes the following coenzymes (i) and (ii):

(i) a first coenzyme selected from the group consisting of thionicotinamide adenine dinucleotide phosphate or its analog (thio-NADP compound) and thionicotinamide adenine dinucleotide or its analog (thio-NAD compound), and (ii) a second coenzyme selected from the group consisting of nicotinamide adenine dinucleotide phosphate or its analog (NADP compound) and nicotinamide adenine dinucleotide or its analog (NAD compound), and catalyzes the reversible reaction producing acetoacetic acid from D-3-hydroxybutyric acid as a substrate;

(2) $A_1$ (defined hereinbelow);

(3) at least one coenzyme selected from $B_1$ (defined hereinbelow) and $B_2$ (defined hereinbelow); and (4) a second dehydrogenase which does not react with D-3-hydroxybutyric acid but acts to promote the reaction for converting $B_2$ to $B_1$, in combination with a substrate for the second dehydrogenase, wherein $A_1$ is a thio-NADP compound, a thio-NAD compound, an NADP compound or an NAD compound; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; $B_2$ is an oxidized form of $B_1$.

In still a further aspect of the present invention, there is provided an analytical reagent for use in the quantitative determination of at least one ketone body selected from the group consisting of D-3-hydroxybutyric acid and acetoacetic acid, which comprises:

(1) a D-3-hydroxybutyrate dehydrogenase as a first dehydrogenase which utilizes the following coenzymes (i) and (ii):

(i) a first coenzyme selected from the group consisting of thionicotinamide adenine dinucleotide phosphate or its analog (thio-NADP compound) and thionicotinamide adenine dinucleotide or its analog (thio-NAD compound), and (ii) a second coenzyme selected from the group consisting of nicotinamide adenine dinucleotide phosphate or its analog (NADP compound) and nicotinamide adenine dinucleotide or its analog (NAD compound), and catalyzes the reversible reaction producing acetoacetic acid from D-3-hydroxybutyric acid as a substrate;

(2) at least one coenzyme selected from $A_1$ (defined hereinbelow) and $A_2$ (defined hereinbelow); and (3) $B_1$ (defined hereinbelow);

(5) a third dehydrogenase which does not react with D-3-hydroxybutyric acid but acts to promote the reaction for converting $A_2$ to $A_1$, in combination with a substrate for the third dehydrogenase, wherein $A_1$ is a thio-NADP compound, a thio-NAD compound, an NADP compound or an NAD compound; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; $A_2$ is a reduced form of $A_1$.

The D-3-hydroxybutyrate dehydrogenase to be used in the method of the present invention is defined as a dehydrogenase which utilizes (i) a first coenzyme selected from the group consisting of a thio-NADP compound and a thio-NAD compound, and (ii) a second coenzyme selected from an NADP compound and an NAD compound, and catalyzes the reversible reaction producing acetoacetic acid from D-3-hydroxybutyric acid as a substrate. A typical example of he above-mentioned reversible reaction is represented by the following formula:

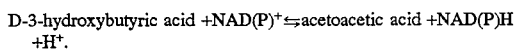

D-3-hydroxybutyric acid +NAD(P)$^+$ ⇌ acetoacetic acid +NAD(P)H +H$^+$.

Specific examples of such D-3-hydroxybutyrate dehydrogenases as defined above include: those derived from Pseudomonas sp., (manufactured by Toyobo Co., Ltd., Japan), Rhodopseudomonas spheroides, Rhodospirillum rubrum, Pseudomonas lemoignei and animal tissues, e.g., mitochondria derived from rat liver (see, Enzyme catalogue, No. 350.HBD, Toyobo Co., Ltd., Japan; Enzyme Handbook, p.11–12, Asakura Shoten, Japan, 1982; Biochem. J., vol. 102, p.423–431, 1967; J. Biol. Chem., vol. 237, p.603–607, 1962; and Methods in Enzymol., vol. 14, p.227–231, Japan, 1969). Among these, a D-3-hydroxybutyrate dehydrogenase derived from Pseudomonas sp. which can be used in combination with either a (thio)NAD compound or a (thio)NADP compound as a coenzyme, is especially preferable. With respect to the D-3-hydroxybutyrate dehydrogenase derived from Pseudomonas sp., when the activity exerted with use of NAD is taken as 100%, the relative activity exerted with use of NADP is 4.74% (Enzyme Catalogue, No. 350.HBD, Toyobo Co., Ltd., Japan) and the relative activity exerted with use of thio-NAD is about 10%; and when the activity exerted with use of NADP is taken as 100%, the relative activity exerted with use of thio-NADP is about 10%. With respect to the D-3-hydroxybutyrate dehydrogenases of other origins, many of these enzymes are used in combination with an NAD compound and a thio-NAD compound. Such dehydrogenases also can be used in appropriate systems.

In the present invention, coenzymes $A_1$ and $B_2$ are appropriately selected from the group consisting of a thio-NADP compound, a thio-NAD compound, an NADP compound and an NAD compound in accordance with the designed reaction scheme. Examples of thio-NADP compounds and thio-NAD compounds include thionicotinamide adenine dinucleotide phosphate (thio-NADP) and thionicotinamide hypoxanthine dinucleotide phosphate; and thionicotinamide adenine dinucleotide (thio-NAD) and thionicotinamide hypoxanthine dinucleotide. Examples of NADP compounds and NAD compounds include nicotinamide adenine dinucleotide phosphate (NADP), acetylpyridine adenine dinucleotide phosphate (acetyl NADP), acetylpyridine hypoxanthine dinucleotide phosphate, nicotinamide hypoxanthine dinucleotide phosphate (deamino NADP); and nicotinamide adenine dinucleotide (NAD), acetylpyridine adenine dinucleotide (acetyl NAD), acetylpyridine hypoxanthine dinucleotide and nicotinamide hypoxanthine dinucleotide (deamino NAD). Hereinafter, reduced types of these coenzymes are referred to, for example, as a thio-NADPH compound, a thio-NADH compound, an NADPH compound and an NADH compound.

In the present invention, for example, when $A_1$ is a thio-NAD(P) compound, $B_1$ is an NAD(P)H compound, and when $A_1$ is an NAD(P) compound, $B_1$ is a thio-NAD(P)H compound.

When the D-3-hydroxybutyrate dehydrogenase to be used is capable of reacting only with NAD type coenzymes, i.e., a thio-NAD compound and an NAD compound, appropriate NAD type coenzymes are selected from the above-mentioned thio-NAD compounds and NAD compounds. When the D-3-hydroxybutyrate dehydrogenase to be used is capable of reacting only with NADP type coenzymes, i.e., a thio-NADP compound and an NADP compound, appropriate NADP coenzymes are selected from the above-mentioned thio-NADP compounds and NADP compounds. When the D-3-hydroxybutyrate dehydrogenase to be used is capable of reacting with either NAD type coenzymes or NADP type coenzymes, appropriate NAD type or NADP type coenzymes are selected from the above-mentioned thio-NAD compounds, thio-NADP compounds, NAD compounds and NADP compounds.

In the method of the present invention, component (2) (coenzyme $A_1$) and component (3) (coenzyme $B_1$) are used in excess amounts relative not only to the total amount of D-3-hydroxybutyric acid and acetoacetic acid, but also the respective Km (Michaelis constant) values of component (1) (D-3-hydroxybutyrate dehydrogenase) for components (2) and (3). It is especially preferred to use each of components (2) and (3) in a molar amount which is 20 to 10,000 times the total mole of D-3-hy droxybutyric acid and acetoacetic acid.

As mentioned above, in another aspect of the present invention, there is provided an analytical reagent for use in the above-mentioned quantitative determination. In the analytical reagent of the present invention, the concentration of each of component (2) ($A_1$) and component (3) ($B_1$) is 0.02 to 100 mM, preferably 0.05 to 20 mM, and the concentration of component (1) (D-3-hydroxybutyrate dehydrogenase) is 5 to 1,000 U/ml, preferably 20 to 400 U/ml. However, an appropriate concentration of each of components (1), (2) and (3) in the analytical reagent is varied depending on the type of a biological sample to be tested and, if desired, these components can be used in larger amounts.

In the present invention, when $B_2$ functions also as a coenzyme for a certain dehydrogenase other than the D-3-hydroxybutyrate dehydrogenase of the cycling reaction (I), which certain dehydrogenase does not react with D-3-hydroxybutyric acid but acts to promote the reaction for converting $B_2$ to $B_1$ in cooperation with a substrate for the certain dehydrogenase, such a certain dehydrogenase (which is hereinafter frequently referred to as "second dehydrogenase") can also be additionally incorporated together with a substrate therefor (second dehydrogenase is referred to also as "component (4)") into the reagent for effecting the following cycling reaction (II):

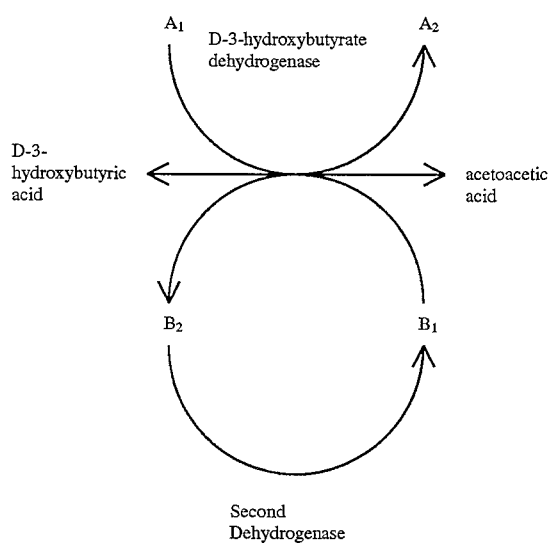

wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; or an NAD compound; and $B_2$ is an oxidized form of $B_1$.

In the above reaction system, as the second dehydrogenase, a dehydrogenase which does substantially not react with $A_1$ but acts to promote the reaction for converting $B_2$ to $B_1$, is chosen. Alternatively, by choosing reaction conditions under which the second dehydrogenase does not react with $A_1$, the objective can be attained. For example, there can be chosen appropriate $A_1$–$B_2$ amount relationship conditions under which the second dehydrogenase does substantially not react with $A_1$. The quantitative determination of the target chemical substance participating in reaction (II), can be achieved by measuring a change in the amount of $A_2$ [which is caused for a predetermined period of time during reaction (II)].

The second dehydrogenase can be advantageously used in order to regenerate $B_1$, so that the amount of $B_1$ to be used in the analytical reaction can be reduced. This is particularly useful when $B_1$ is an expensive compound. It is also possible to use $B_2$ alone or a mixture of $B_1$ and $B_2$ at the initiation of the reaction. For conducting reaction (II), an amount of at least one coenzyme selected from $B_1$ and $B_2$ is preferably not larger than 1/10 mole per mole of $A_1$, although the amount is not particularly limited.

In practicing the above method for quantitative determination of the present invention using a second dehydrogenase as component (4), $A_1$ is used in a concentration of 0.02 to 100 mM, preferably 0.05 to 20 mM. $B_2$ and/or $B_1$ is used in a concentration of 0.05 to 5,000 µM, preferably 5 to 500 µM. A D-3-hydroxybutyrate dehydrogenase as the first dehydrogenase is used in a concentration of 5 to 1000 U/ml, preferably 20 to 400 U/ml. The concentration of the second dehydrogenase (U/ml) can be 20 times or more the Km value (unit: mM) thereof for $B_2$, e.g., 1 to 100 U/ml. The substrate for the second dehydrogenase can be used in a stoichiometrically excess amount, for example, 0.05 to 20 mM. The amounts of the components of the reagent for the cycling reaction can be varied depending on the type of a biological sample to be tested. The amount exceeding the above can also be employed.

As examples of combinations of second dehydrogenases and substrates therefor, the following combinations can be mentioned. When $B_2$ is an NAD compound or a thio-NAD compound, there can be mentioned combinations of: alcohol dehydrogenase (EC 1.1.1.1) and ethanol; glycerol dehydrogenase (EC 1.1.1.6) derived from E. coli and glycerol; glycerol-3-phosphate dehydrogenase (EC 1.1.1.8) derived from rabbit muscle and L-glycerol-3-phosphate; malate dehydrogenase (EC 1.1.1.37) derived from pig or bovine heart and L-malic acid; and glyceraldehyde phosphate dehydrogenase (EC 1.1.1.12) derived from rabbit muscle, liver, yeast or E. coli, D-glyceraldehyde phosphate and phosphoric acid. When $B_2$ is an NADP compound or a thio-NADP compound, there can be mentioned combinations of: glucose-6-phosphate dehydrogenase (EC 1.1.1.49) derived from yeast and D-glucose-6-phosphate; isocitrate dehydrogenase (EC 1.1.1.42) derived from yeast or pig heart and isocitric acid; glyoxylate dehydrogenase (EC 1.2.1.17) derived from Pseudomonas oxalaticus, CoA and glyoxylic acid; phosphogluconate dehydrogenase (EC 1.1.1.44) derived from rat liver, beer yeast or E. coli and 6-phospho-D-gluconic acid; glyceraldehyde phosphate dehydrogenase (EC 1.2.1.13) derived from plant chlorophyll, D-glyceraldehyde-3-phosphate and phosphoric acid; and benzaldehyde dehydrogenase (EC 1.2.1.7) derived from Pseudomonas fluorescens and benzaldehyde.

Furthermore, in the present invention, when $A_2$ functions also as a coenzyme for a certain dehydrogenase other than the D-3-hydroxybutyrate dehydrogenase of the reaction (I) and the second dehydrogenase of the reaction (II), which certain dehydrogenase does not react with D-3-hydroxybutyric acid but acts to promote the reaction for converting $A_2$ to $A_1$ in cooperation with a substrate for the certain dehydrogenase, such a certain dehydrogenase (which is hereinafter frequently referred to as "third dehydrogenase") can also be additionally incorporated together with a substrate therefor (third dehydrogenase is referred to as "component (5)") into the reagent for effecting the following cycling reaction (III):

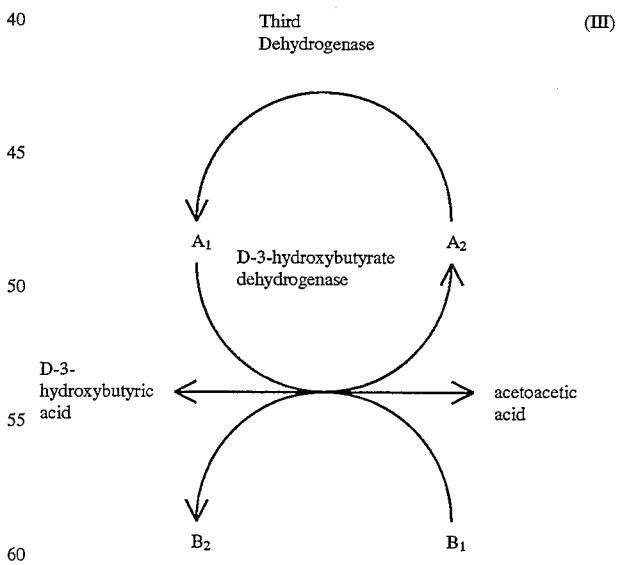

wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized form of $B_1$.

In the above reaction system, as the third dehydrogenase, a dehydrogenase which does substantially not react with $B_1$ but acts to promote the reaction for converting $A_2$ to $A_1$, is chosen. Alternatively, by choosing reaction conditions under which the third dehydrogenase does not react with $B_1$, the objective can be attained. For example, there can be chosen appropriate $B_1$–$A_2$ amount relationship conditions under which the third dehydrogenase does substantially not react with $B_1$. The quantitative determination of the target chemical substance participating in reaction (III), can be achieved by measuring a change in the amount of $B_1$ [which is caused for a predetermined period of time during reaction (III)].

The third dehydrogenase can be advantageously used in order to regenerate $A_1$, so that the amount of $A_1$ to be used in the analytical reaction can be reduced. This is particularly useful when $A_1$ is an expensive compound. It is also possible to use $A_2$ alone or a mixture of $A_1$ and $A_2$, at the initiation of the reaction. For conducting reaction (III), an amount of at least one coenzyme selected from $A_1$ and $A_2$ is preferably not larger than $\frac{1}{10}$ mole per mole of $B_1$, although the amount is not particularly limited.

In practicing the above method for quantitative determination of the present invention using a third dehydrogenase as component (5), $B_1$ is used in a concentration of 0.02 to 100 mM, preferably 0.05 to 20 mM. $A_2$ and/or $A_1$ is used in a concentration of 0.05 to 5,000 μM, preferably 5 to 500 μM. D-3-hydroxybutyrate dehydrogenase as the first dehydrogenase is used in a concentration of 5 to 1000 U/ml, preferably 20 to 400 U/ml. The concentration of the third dehydrogenase (U/ml) can be 20 times or more the Km value (unit: mM) thereof for $A_2$, e.g., 1 to 100 U/ml. The substrate for the third dehydrogenase can be used in a stoichiometrically excess amount, for example, 0.05 to 20 mM. The amounts of the components of the reagent for the cycling reaction can be varied depending on the type of a biological sample to be tested. The amounts exceeding the above can also be employed.

As Examples of combinations of third dehydrogenases and substrates therefor, the following combinations can be mentioned. When $A_1$ is an NAD compound or a thio-NAD compound, there can be mentioned combination of: alcohol dehydrogenase (EC 1.1.1.1) and acetaldehyde; glycerol dehydrogenase (EC 1.1.1.6) derived from E. coli and dihydroxyacetone; glycerol-3-phosphate dehydrogenase (EC 1.1.1.8) derived from rabbit muscle and dihydroxyacetone phosphate; malate dehydrogenase (EC 1.1.1.37) derived from pig or bovine heart and oxaloacetic acid; and glyceraldehyde phosphate dehydrogenase (EC 1.1.1.12) derived from rabbit muscle, liver, yeast or E. coli and 1,3-diphospho-D-glycerate. When $A_1$ is an NADP compound or a thio-NADP compound, there can be mentioned combinations of: glucose-6-phosphate dehydrogenase (EC 1.1.1.49) derived from yeast and D-glucono-S-lactone-6-phosphate; and glyceraldehyde phosphate dehydrogenase (EC 1.2.1.13) derived from plant chlorophyll and 1,3-diphospho-D-glyceric acid.

In the method of the present invention, types of coenzymes $A_1$ and $B_1$ can be appropriately selected, taking into consideration the relative activities and the like of the coenzymes, and pH conditions for the forward and reverse reactions can also be appropriately selected so that the enzymatic cycling reaction proceeds efficiently.

In practicing the method for the quantitative determination of D-3-hydroxybutyric acid and acetoacetic acid in a biological sample by using the analytical reagent of the present invention, 0.001 to 1 ml of the biological sample can be added to an aqueous composition containing the above-defined components (1) to (3), (1) to (4), or (1) to (3) and (5), and the resultant solution is reacted at about 37° C. Then, a change in the absorbance at a wavelength specific for coenzyme $A_2$ or $B_1$ is measured, which is observed with respect to the reaction mixture as between predetermined two time points during the reaction (e.g., between 3 and 4 minutes after the start of the reaction, or between 3 and 8 minutes after the start of the reaction). The period between such two time points during the reaction can be varied in the range from several minutes to several tens of minutes, depending on the type of a biological sample and the type of a target chemical substance contained therein. For example, when $A_2$ is a thio-NADH compound and $B_1$ is an NADH compound, either the produced $A_2$ is determined in terms of the change in absorbance at 400 nm, or the consumed $B_1$ is determined in terms of the change in absorbance at 340 nm. The thus obtained change in absorbance reflecting the amount of the target chemical substance is applied to a calibration curve which has been prepared with respect to a standard sample containing D-3-hydroxybutyric acid or acetoacetic acid, to thereby determine the amount of the target chemical substance. By the method of the present invention, it becomes possible to realize a real-time quantitative determination of D-3-hydroxybutyric acid and acetoacetic acid in a biological sample.

Further, according to the method of the present invention, when a biological sample to be subjected to quantitative determination is a sample which usually contains D-3-hydroxybutyric acid and acetoacetic acid, for example, serum or plasma, the total amount of D-3-hydroxybutyric acid and acetoacetic acid, i.e., the total amount of ketone bodies, can be efficiently obtained with a single operation. Any method achieving such excellent performances has never been known in the art. Such excellent performances have for the first time been realized by the method of the present invention. In the method of the present invention, both of D-3-hydroxybutyric acid and acetoacetic acid are skillfully introduced directly to an enzymatic cycling reaction system, based on a knowledge that both of D-3-hydroxybutyric acid and acetoacetic acid are substrates for a D-3-hydroxybutyrate dehydrogenase.

Furthermore, according to the present invention, either one of D-3-hydroxybutyric acid and acetoacetic acid can be separately determined by pretreating a biological sample containing both of the above-mentioned ketone bodies with an enzyme which is capable of reacting only with one of the above-mentioned two types of ketone bodies and subsequently introducing the pretreated sample to the specific enzymatic cycling reaction of the method of the present invention. For example, when determination of only D-3-hydroxybutyric acid among D-3-hydroxybutyric acid and acetoacetic acid contained in a biological sample (e.g., serum and plasma) is intended, the sample is pretreated with an acetoacetate decarboxylase (EC 4.1.1.4) to convert the acetoacetic acid to acetone and carbon dioxide, thus eliminating the acetoacetic acid. Then, the D-3-hydroxybutyric acid in the biological sample is quantitatively determined according to the method of the present invention utilizing the enzymatic cycling reaction catalyzed by a D-3-hydroxybutyrate dehydrogenase. Thereafter, the acetoacetic acid can be quantitatively determined by subtracting the amount of the D-3-hydroxybutyric acid from the previously measured total amount of the ketone bodies.

Furthermore, it should be noted that the method of the present invention is so designed that the target chemical substance (i.e., at least one ketone body selected from the group consisting of D-3-hydroxybutyric acid and acetoacetic acid) itself participates in the enzymatic cycling reaction. Therefore, the determination of the target chemical substance by the method of the present invention is less influenced by other substances present in the sample, so that the desired determination can be easily, simply done by rate assay without requiring any blank assay of the sample.

With respect to the determination of $A_2$ or $B_1$, other known methods can be used instead of the measurement of absorbances described above.

Best Mode for Carrying Out the Invention

Hereinbelow, the present invention will be illustrated with reference to the following Examples, which however should not be construed as limiting the scope of the present invention.

EXAMPLE 1

| Reagent | |
|---|---|
| 100 mM | Tris-HCl buffer (pH 8.5) |
| 0.1 mM | reduced NAD (manufactured by Oriental Yeast Co., Ltd., Japan) |
| 4 mM | thio-NAD (manufactured by Sigma Co., Ltd., U.S.A.) |
| 45 U/ml | D-3-hydroxybutyrate dehydrogenase (derived from Pseudomonas sp. and manufactured by Toyobo Co., Ltd., Japan) |

Procedure 1 ml of the above reagent was placed in each of six cuvettes and heated to 37° C. To the respective cuvettes were individually added 20 µl each of six types of aqueous D-3-hydroxybutyric acid solutions respectively having concentrations of 0, 10, 20, 30, 40 and 50 µM. The resultant mixtures in the respective cuvettes were individually allowed to react at 37° C. With respect to each of respective samples taken from the reaction mixtures in the six cuvettes, absorbances at 400 nm were measured 2 minutes and 5 minutes after the start of the reaction, and a change in absorbance as between the above two time points was calculated with respect to each of the samples. Results are shown in FIG. 1, which demonstrates the presence of good linearity in the relationship between the change (difference) in absorbance (with respect to the reaction mixture, as between 2 and 5 minutes after the start of the reaction) and the D-3-hydroxybutyric acid concentration.

EXAMPLE 2

Figure 2:
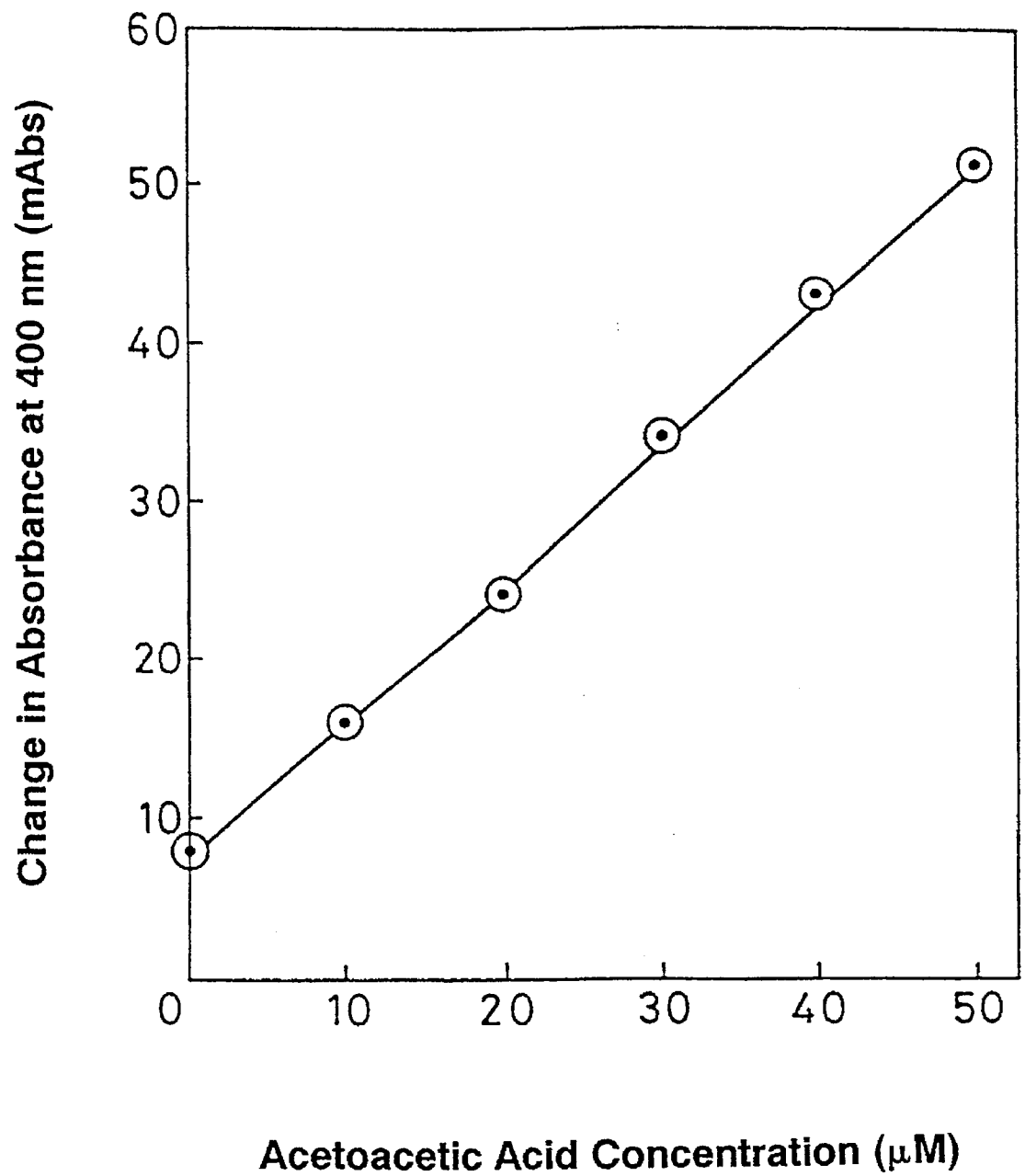
FIG. 2 is a graph showing the results of the rate assay of acetoacetic acid at a wavelength of 400 nm conducted in Example 2.

Substantially the same procedure was repeated as in Example 1 except that aqueous acetoacetic acid solutions were used in place of the aqueous D-3-hydroxybutyric acid solutions. Results are shown in FIG. 2, which demonstrates the presence of good linearity in the relationship between the change (difference) in absorbance (with respect to the reaction mixture, as between 2 and 5 minutes after the start of the reaction) and the acetoacetic acid concentration.

EXAMPLE 3

| Reagent | |
|---|---|
| 100 mM | Tris-HCl buffer (pH 8.5) |
| 0.1 mM | reduced NAD (manufactured by Oriental Yeast Co., Ltd., Japan) |
| 5 mM | thio-NAD (manufactured by Sigma Co., Ltd., U.S.A.) |
| 60 U/ml | D-3-hydroxybutyrate dehydrogenase (derived from Pseudomonas sp. and manufactured by Toyobo Co., Ltd., Japan) |
| 0.2% | Triton X-100 (manufactured by Sigma Co., Ltd., U.S.A.) |

Procedure 1 ml of the above reagent was placed in each of four cuvettes and heated to 37° C. To the respective cuvettes were individually added 20 µl each of four different types of sera derived from healthy human beings. The resultant mixtures in the respective cuvettes were individually allowed to react at 37° C. With respect to each of respective samples taken from the reaction mixtures in the four cuvettes, absorbances at 400 nm were measured 2 minutes and 5 minutes after the start of the reaction, and a change in absorbance as between the above two time points was calculated with respect to each of the samples.

On the other hand, substantially the same procedure as mentioned above was repeated except that an aqueous solution having a D-3-hydroxybutyric acid concentration of 50 µM as a standard sample and distilled water were individually used instead of the serum samples. Absorbance values obtained 2 minutes and 5 minutes after the start of the reaction with respect to the distilled water were taken as respective reagent blanks at the above two time points, and were subtracted from the absorbance values obtained with respect to the serum samples as well as the standard sample. Using the absorbance data of the standard sample and the distilled water, a calibration curve was obtained.

The change in absorbance as between the above two time points, which was obtained with respect to each of the serum samples, was applied to the above-mentioned calibration curve, to thereby determine the total concentration of the ketone bodies (D-3-hydroxybutyric acid and acetoacetic acid). Results are shown in Table 1.

TABLE 1

| | Total concentration of the ketone bodies (D-3-hydroxybutyric acid + acetoacetic acid) (µM) |
|---|---|
| Serum 1 | 78.3 |
| Serum 2 | 48.7 |
| Serum 3 | 53.4 |
| Serum 4 | 62.9 |

EXAMPLE 4

| Reagent (I) | |
|---|---|
| 10 mM | phosphate buffer (pH 6.0) |
| 0.2% | Triton X-100 (manufactured by Sigma Co., Ltd., U.S.A.) |
| 10 U/ml | acetoacetate decarboxylase (derived from *Bacillus polymyxa* and manufactured by Wako Pure Chemical Industries, Ltd., Japan) |

| Reagent (II) | |
|---|---|
| 200 mM | Tris-HCl buffer (pH 9.0) |
| 0.2 mM | reduced NAD (manufactured by Oriental Yeast Co., Ltd., Japan) |

| | |
|---|---|
| 10 mM | thio-NAD (manufactured by Sigma Co., Ltd., U.S.A.) |
| 120 U/ml | D-3-hydroxybutyrate dehydrogenase (derived from Pseudomonas sp. and manufactured by Toyobo Co., Ltd., Japan) |

Procedure 0.45 ml of the above reagent (I) was placed in each of four cuvettes and heated to 37° C. To the respective cuvettes were individually added 20 μl each of four different types of sera which were the same as those used in Example 3. The resultant mixtures in the respective cuvettes were individually allowed to react at 37° C for 5 minutes, thereby eliminating acetoacetic acid originally present in the samples. 0.05 ml of 0.2N hydrochloric acid was added to each of the resultant mixture to thereby deactivate the acetoacetate decarboxylase. Then, to the respective cuvettes were individually added 0.5 ml of the above reagent (II). The resultant mixtures in the respective cuvettes were individually allowed to react at 37° C. With respect to each of respective samples taken from the mixtures in the four cuvettes, absorbances at 400 nm were measured 2 minutes and 5 minutes after the start of the reaction, and a change in absorbance as between the above two time points was calculated with respect to each of the samples.

On the other hand, substantially the same procedure as mentioned above was repeated except that an aqueous solution having a D-3-hydroxybutyric acid concentration of 50 μM as a standard sample and distilled water were individually used instead of serum samples. Absorbance values obtained 2 minutes and 5 minutes after the start of the reaction with respect to the distilled water were taken as respective reagent blanks at the above two time points, and were subtracted from the absorbance values obtained with respect to the serum samples as well as the standard sample. Using the absorbance data of the standard sample and the distilled water, a calibration curve was obtained. The change in absorbance as between 2 minutes and 5 minutes after the start of the reaction, which was obtained with respect to each of the serum samples, was applied to the above-mentioned calibration curve to thereby determine the concentration of D-3-hydroxybutyric acid. Further, with respect to each of the samples, the value of the above-obtained concentration of D-3-hydroxybutyric acid in the sample was subtracted from the total concentration of ketone bodies obtained in Example 3 above, thereby obtaining the concentration of acetoacetic acid in the sample. Results are shown in Table 2.

TABLE 2

| | D-3-hydroxybutyric acid (μM) | Acetoacetic acid (μM) | Total concentration of ketone bodies (μM) |
|---|---|---|---|
| Serum 1 | 37.4 | 40.9 | 78.3 |
| Serum 2 | 22.5 | 26.2 | 48.7 |
| Serum 3 | 26.1 | 27.3 | 53.4 |
| Serum 4 | 28.0 | 34.9 | 62.9 |

EXAMPLE 5

| | Reagent |
|---|---|
| 40 mM | Na$_2$CO$_3$—NaHCO$_3$ buffer (pH 10.0) |
| 20 mM | NADP (manufactured by Oriental Yeast Co., Ltd., Japan) |
| 50 mM | thio-NAD (manufactured by Sigma Co., Ltd., U.S.A.) |
| 0.4 M | ethanol |
| 30 U/ml | alcohol dehydrogenase (manufactured by Oriental Yeast Co., Ltd., Japan) |
| 350 U/ml | D-3-hydroxybutyrate dehydrogenase (derived from Pseudomonas sp. and manufactured by Toyobo Co., Ltd., Japan) |

Figure 3:
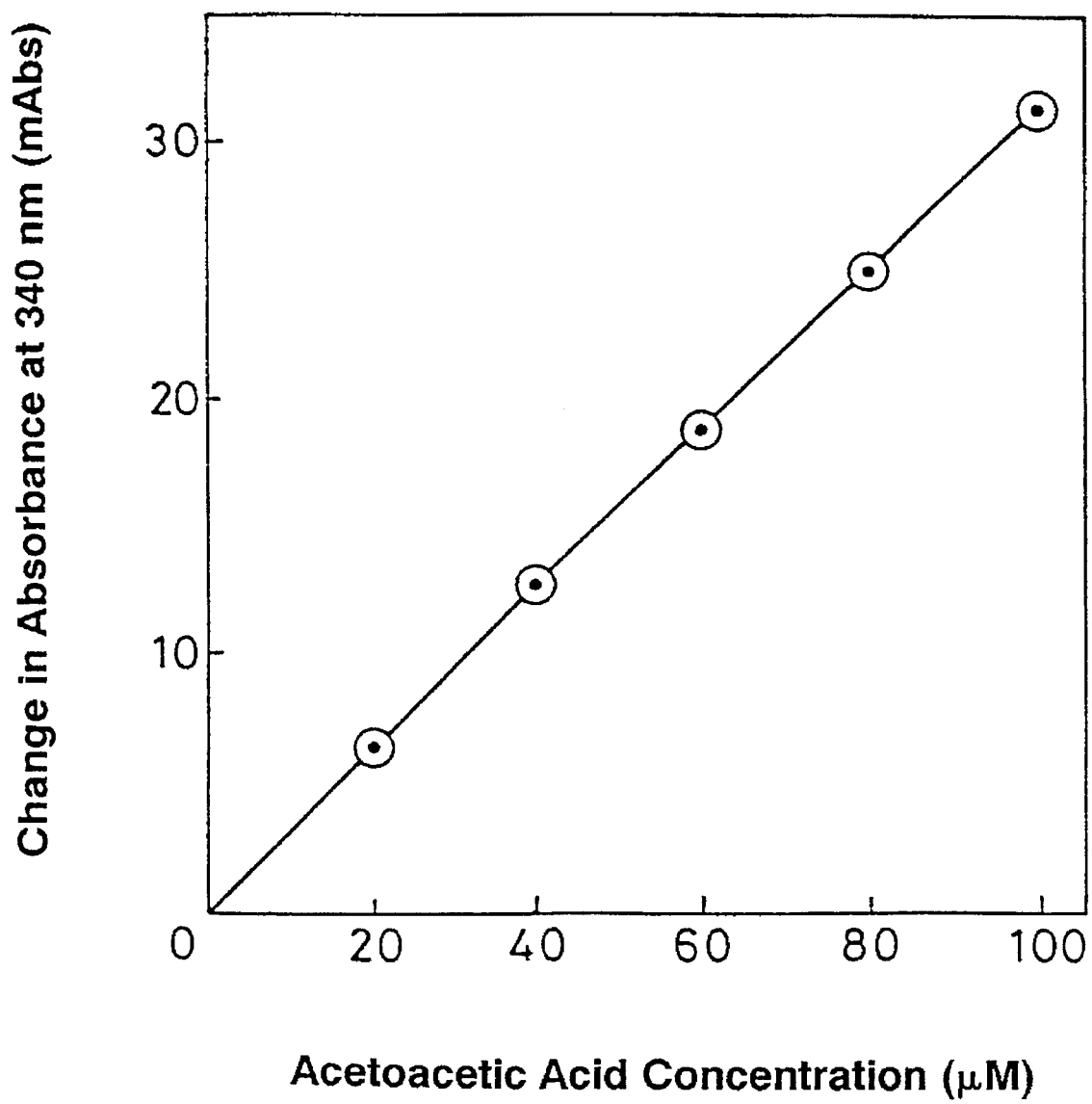
FIG. 3 is a graph showing the results of the rate assay of acetoacetic acid at a wavelength of 340 nm conducted in Example 5.

Procedure 1 ml of the above reagent was placed in each of six cuvettes. To the respective cuvettes were individually added 50 μl each of six types of aqueous acetoacetic acid solutions respectively having concentrations of 0, 20, 40, 60, 80 and 100 μM. The resultant mixtures in the respective cuvettes were individually allowed to react at 37° C. With respect to each of respective samples taken from the reaction mixtures in the six cuvettes, absorbances at 340 nm were measured 3 minutes and 8 minutes after the start of the reaction. Absorbance values obtained 3 minutes and 8 minutes after the start of the reaction with respect to the sample from the cuvette containing the 0 μM concentration solution were taken as reagent blanks, and subtracted from the respective absorbance values obtained with respect to the samples from the remaining five cuvettes, which had different acetoacetic acid concentrations of from 20 to 100 μM as mentioned above. Using the absorption data of the samples from the remaining five cuvettes and the reagent blanks, a change in absorbance as between the above two time points was calculated with respect to each of the samples. Results are shown in FIG. 3, which demonstrates the presence of good linearity in the relationship between the change (difference) in absorbance (with respect to the reaction mixture, as between 3 and 8 minutes after the start of the reaction) and the acetoacetic acid concentration.

EXAMPLE 6

| | Reagent |
|---|---|
| 50 mM | Tris-HCl buffer (pH 8.0) |
| 0.25 mM | reduced NAD (manufactured by Oriental Yeast Co., Ltd., Japan) |
| 50 mM | thio-NAD (manufactured by Sigma Co., Ltd., U.S.A.) |
| 5 mM | dihydroxyacetone phosphate |
| 10 U/ml | glycerol-3-phosphate dehydrogenase (derived from rabbit muscle and manufactured by Boehringer-Mannheim GmbH, Germany) |
| 350 U/ml | D-3-hydroxybutyrate dehydrogenase (derived from Pseudomonas sp. and manufactured by Toyobo Co., Ltd., Japan) |

Figure 4:
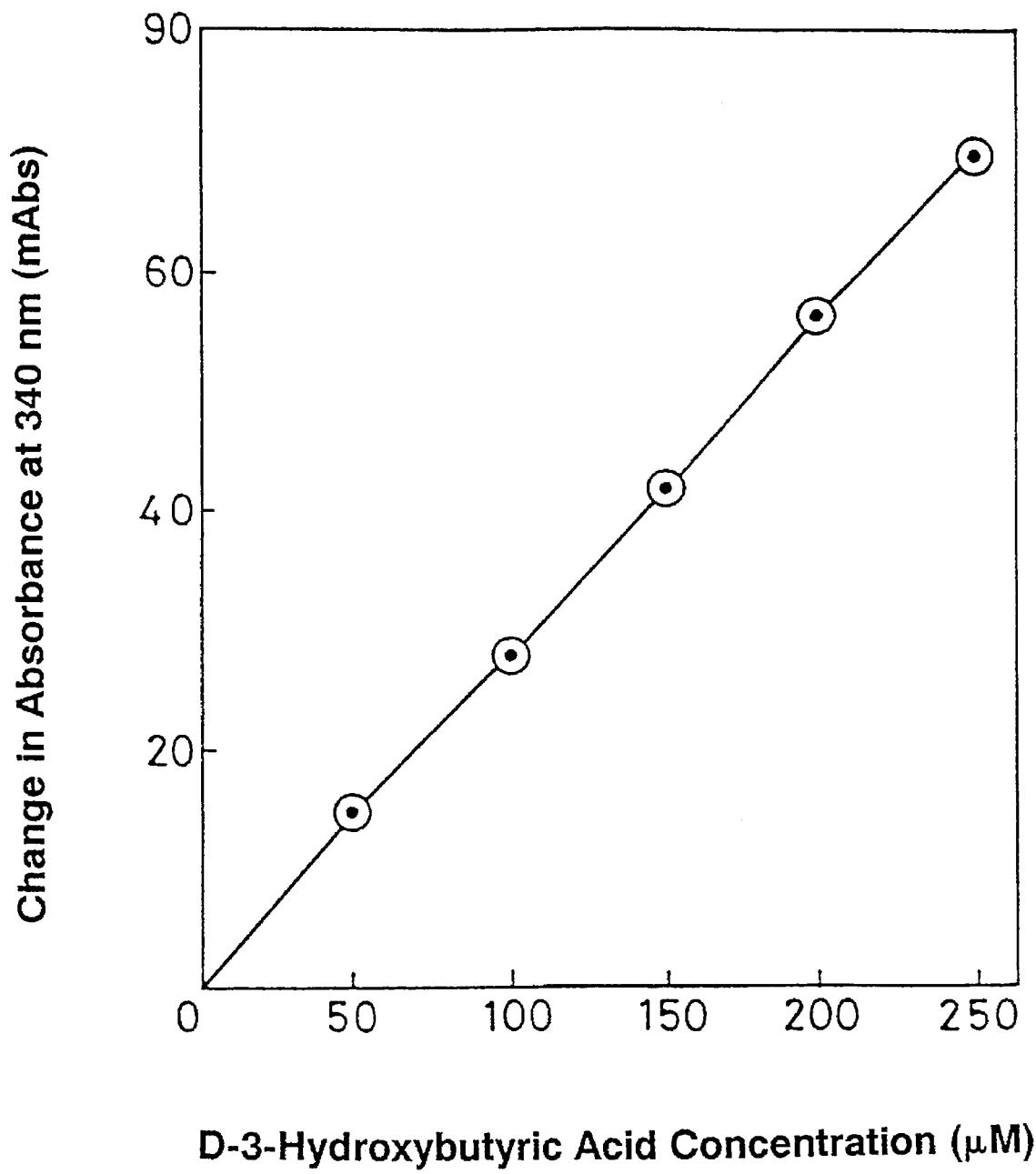
FIG. 4 is a graph showing the results of the rate assay of D-3-hydroxybutyric acid at a wavelength of 340 nm conducted in Example 6.

Procedure 1 ml of the above reagent was placed in each of six cuvettes. To the respective cuvettes were individually added 50 μl each of six types of aqueous acetoacetic acid solutions respectively having concentrations of 0, 50, 100, 150, 200 and 250 μM. The resultant mixtures in the respective cuvettes were individually allowed to react at 37° C. With respect to each of respective samples taken from the reaction mixtures in the six cuvettes, absorbances at 340 nm were measured 3 minutes and 8 minutes after the start of the reaction. Absorbance values obtained 3 minutes and 8 minutes after the start of the reaction with respect to the sample from the cuvette containing the 0 μM concentration solution were taken as reagent blanks, and subtracted from the respective absorbance values obtained with respect to the samples from the remaining five cuvettes, which had different acetoacetic acid concentrations of from 50 to 250 μM as mentioned above. Using the absorption data of the samples from the remaining five cuvettes and the reagent blanks, a change in absorbance as between the above two time points was calculated with respect to each of the samples. Results are shown in FIG. 4, which demonstrates the presence of good linearity in the relationship between the change (difference) in absorbance (with respect to the reaction mixture, as between 3 and 8 minutes after the start of the reaction) and the acetoacetic acid concentration.

Industrial Applicability

According to the determination method of the present invention, an error in the quantitative determination of D-3-hydroxybutyric acid and acetoacetic acid can be minimized since two types of coenzymes exhibiting absorbances at different absorption wave-lengths are used. Further, the sensitivity of the determination method can be greatly increased due to the utilization of the enzymatic cycling reaction. Thus, the method of the present invention ensures rapidness and accuracy in the determination of D-3-hydroxybutyric acid and acetoacetic acid, even with the use of a small quantity of a biological sample.

We claim:

1. A method for the quantitative determination of at least one ketone body selected from the group consisting of D-3-hydroxybutyric acid and acetoacetic acid, which consists essentially of:

reacting a biological sample containing at least one ketone body selected from the group consisting of D-3-hydroxybutyric acid and acetoacetic acid with a reagent comprising:
(1) a D-3-hydroxybutyrate dehydrogenase which utilizes the following coenzymes (i) and (ii):
(i) a first coenzyme selected from the group consisting of thionicotinamide adenine dinucleotide phosphate or its analog (thio-NADP compound) and thionicotinamide adenine dinucleotide or its analog (thio-NAD compound), and
(ii) a second coenzyme selected from the group consisting of nicotinamide adenine dinucleotide phosphate or its analog (NADP compound) and nicotinamide adenine dinucleotide or its analog (NAD compound),
and catalyzes the reversible reaction producing acetoacetic acid from D-3-hydroxybutyric acid as a substrate;
(2) $A_1$; and
(3) $B_1$;

said components (1), (2) and (3) participating in the following cycling reaction:

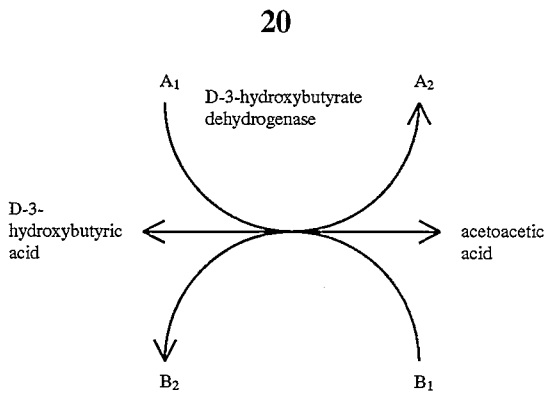

wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized form of $B_1$, wherein the reaction of said biological sample with said reagent is conducted under conditions adapted for the enzymatically catalytic and cycling reaction, thereby effecting said cycling reaction; and measuring and correlating a change in the amount of $A_2$ or $B_1$ to the quantity of said at least one ketone body.

2. The method according to claim 1, wherein said thio-NADP compound is thionicotinamide adenine dinucleotide phosphate (thio-NADP) or thionicotinamide hypoxanthine dinucleotide phosphate.

3. The method according to claim 1, wherein said thio-NAD compound is thionicotinamide adenine dinucleotide (thio-NAD) or thionicotinamide hypoxanthine dinucleotide.

4. The method according to claim 1, wherein said NADP compound is selected from the group consisting of nicotinamide adenine dinucleotide phosphate (NADP), acetylpyridine adenine dinucleotide phosphate (acetyl-NADP), acetylpyridine adenine hypoxanthine dinucleotide phosphate and nicotinamide hypoxanthine dinucleotide phosphate (deamino-NADP).

5. The method according to claim 1, wherein said NAD compound is selected from the group consisting of nicotinamide adenine dinucleotide (NAD), acetylpyridine adenine dinucleotide (acetyl-NAD), acetylpyridine adenine hypoxanthine dinucleotide and nicotinamide hypoxanthine dinucleotide (deamino-NAD).

6. A method for the quantitative determination of at least one ketone body selected from the group consisting of D-3-hydroxybutyric acid and acetoacetic acid, which consists essentially of:

reacting a biological sample containing at least one ketone body selected from the group consisting of D-3-hydroxybutyric acid and acetoacetic acid with a reagent comprising:
(1) a D-3-hydroxybutyrate dehydrogenase as a first dehydrogenase which utilizes the following coenzymes (i) and (ii):
(i) a first coenzyme selected from the group consisting of thionicotinamide adenine dinucleotide phosphate or its analog (thio-NADP compound) and thionicotinamide adenine dinucleotide or its analog (thio-NAD compound), and
(ii) a second coenzyme selected from the group consisting of nicotinamide adenine dinucleotide phosphate or its analog (NADP compound) and nicotinamide adenine dinucleotide or its analog (NAD compound), and catalyzes the reversible reaction producing acetoacetic acid from D-3-hydroxybutyric acid as a substrate;

(2) $A_1$;

(3) at least one coenzyme selected from $B_1$ and $B_2$; and (4) a second dehydrogenase which does not react with D-3-hydroxybutyric acid but acts to promote the reaction for converting $B_2$ to $B_1$ in the following cycling reaction, in combination with a substrate for said second dehydrogenase:

said components (1), (2), (3) and (4) participating in the following cycling reaction:

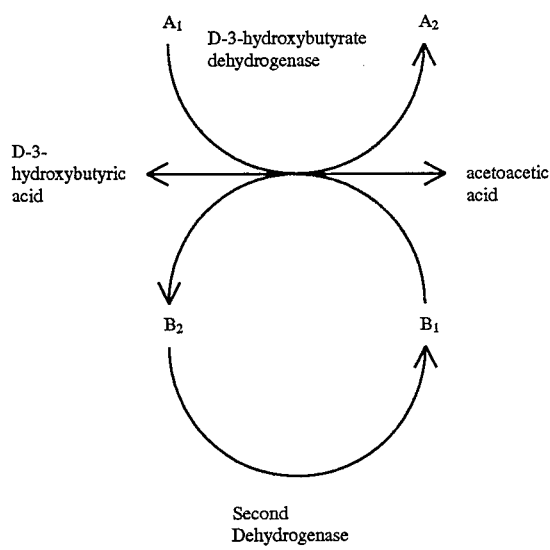

wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; $B_2$ is an oxidized form of $B_1$; and $B_2 \rightarrow B_1$ represents an enzymatic reaction producing $B_1$ from coenzyme $B_2$ under the action of said second dehydrogenase, wherein the reaction of said biological sample with said reagent is conducted under conditions adapted for the enzymatically catalytic and cycling reaction, thereby effecting the cycling reaction; and measuring and correlating a change in the amount of $A_2$ to the quantity of said at least one ketone body.

7. The method according to claim 6, wherein said thio-NADP compound is thionicotinamide adenine dinucleotide phosphate (thio-NADP) or thionicotinamide hypoxanthine dinucleotide phosphate.

8. The method according to claim 6, wherein said thio-NAD compound is thionicotinamide adenine dinucleotide (thio-NAD) or thionicotinamide hypoxanthine dinucleotide.

9. The method according to claim 6, wherein said NADP compound is selected from the group consisting of nicotinamide adenine dinucleotide phosphate (NADP), acetylpyridine adenine dinucleotide phosphate (acetyl-NADP), acetylpyridine adenine hypoxanthine dinucleotide phosphate and nicotinamide hypoxanthine dinucleotide phosphate (deamino-NADP).

10. The method according to claim 6, wherein said NAD compound is selected from the group consisting of nicotinamide adenine dinucleotide (NAD), acetylpyridine adenine dinucleotide (acetyl-NAD), acetylpyridine adenine hypoxanthine dinucleotide and nicotinamide hypoxanthine dinucleotide (deamino-NAD).

11. A method for the quantitative determination of at least one ketone body selected from the group consisting of D-3-hydroxybutyric acid and acetoacetic acid, which consists essentially of:

reacting a biological sample containing at least one ketone body selected from the group consisting of D-3-hydroxybutyric acid and acetoacetic acid with a reagent comprising:

(1) a D-3-hydroxybutyrate dehydrogenase as a first dehydrogenase which utilizes the following coenzymes (i) and (ii):

(i) a first coenzyme selected from the group consisting of thionicotinamide adenine dinucleotide phosphate or its analog (thio-NADP compound) and thionicotinamide adenine dinucleotide or its analog (thio-NAD compound), and (ii) a second coenzyme selected from the group consisting of nicotinamide adenine dinucleotide phosphate or its analog (NADP compound) and, nicotinamide adenine dinucleotide or its analog (NAD compound), and catalyzes the reversible reaction producing acetoacetic acid from D-3-hydroxybutyric acid as a substrate;

(2) at least one coenzyme selected from $A_1$ and $A_2$;

(3) $B_1$; and (5) a third dehydrogenase which does not react with D-3-hydroxybutyric acid but acts to promote the reaction for converting $A_2$ to $A_1$, in the following cycling reaction, in combination with a substrate for said third dehydrogenase:

said components (1), (2), (3) and (5) participating in the following cycling reaction:

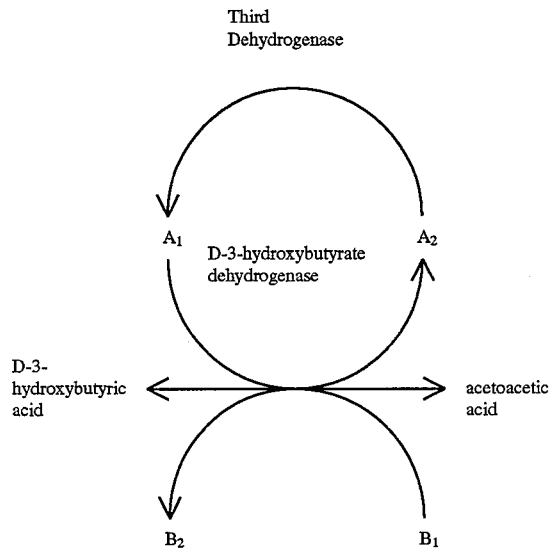

wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$; is a thio-NADP compound or a thio-NAD compound, or a reduced thio-NADP compound or a reduced thio-NAD compound when $A_1$ is an NADP compound or an NAD compound; $B_2$ is an oxidized form of $B_1$; and $A_2 \rightarrow A_1$ represents an enzymatic reaction producing $A_1$ from coenzyme $A_2$ under the action of said third dehydrogenase, wherein the reaction of said biological sample with said reagent is conducted under conditions adapted for the enzymatically catalytic and cycling reaction, thereby effecting the cycling reaction; and measuring and correlating a change in the amount of $B_1$ to the quantity of said at least one ketone body.

12. The method according to claim 11, wherein said thio-NADP compound is thionicotinamide adenine dinucleotide phosphate (thio-NADP) or thionicotinamide hypoxanthine dinucleotide phosphate.

13. The method according to claim 11, wherein said thio-NAD compound is thionicotinamide adenine dinucleotide (thio-NAD) or thionicotinamide hypoxanthine dinucleotide.

14. The method according to claim 11, wherein said NADP compound is selected from the group consisting of nicotinamide adenine dinucleotide phosphate (NADP), acetylpyridine adenine dinucleotide phosphate (acetyl-NADP), acetylpyridine adenine hypoxanthine dinucleotide phosphate and nicotinamide hypoxanthine dinucleotide phosphate (deamino-NADP).

15. The method according to claim 11, wherein said NAD compound is selected from the group consisting of nicotinamide adenine dinucleotide (NAD), acetylpyridine adenine dinucleotide (acetyl-NAD), acetylpyridine adenine hypoxanthine dinucleotide and nicotinamide hypoxanthine dinucleotide (deamino-NAD).

16. An analytical reagent for use in the quantitative determination of at least one ketone body selected from the group consisting of D-3-hydroxybutyric acid and acetoacetic acid, which comprises:

1) a D-3-hydroxybutyrate dehydrogenase which utilizes the following coenzymes (i) and (ii):
    (i) a first coenzyme selected from the group consisting of thionicotinamide adenine dinucleotide phosphate or its analog (thio-NADP compound) and thionicotinamide adenine dinucleotide or its analog (thio-NAD compound), and
    (ii) a second coenzyme selected from the group consisting of nicotinamide adenine dinucleotide phosphate or its analog (NADP compound) and nicotinamide adenine dinucleotide or its analog (NAD compound),
    and catalyzes the reversible reaction producing acetoacetic acid from D-3-hydroxybutyric acid as a substrate;

(2) $A_1$; and (3) $B_1$.

wherein $A_1$ is a thio-NADP compound, a thio-NAD compound, an NADP compound or an NAD compound; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound.

17. An analytical reagent for use in the quantitative determination of at least one ketone body selected from the group consisting of D-3-hydroxybutyric acid and acetoacetic acid, which comprises:

(1) a D-3-hydroxybutyrate dehydrogenase as a first dehydrogenase which utilizes the following coenzymes (i) and (ii):
    (i) a first coenzyme selected from the group consisting of thionicotinamide adenine dinucleotide phosphate or its analog (thio-NADP compound) and thionicotinamide adenine dinucleotide or its analog (thio-NAD compound), and
    (ii) a second coenzyme selected from the group consisting of nicotinamide adenine dinucleotide phosphate or its analog (NADP compound) and nicotinamide adenine dinucleotide or its analog (NAD compound),
    and catalyzes the reversible reaction producing acetoacetic acid from D-3-hydroxybutyric acid as a substrate;

(2) $A_1$;

(3) at least one coenzyme selected from $B_1$ (defined hereinbelow) and $B_2$; and (4) a second dehydrogenase which does not react with D-3-hydroxybutyric acid but acts to promote the reaction for converting $B_2$ to $B_1$, in combination with a substrate for said second dehydrogenase, wherein $A_1$ is a thio-NADP compound, a thio-NAD compound, an NADP compound or an NAD compound; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; $B_2$ is an oxidized form of $B_1$.

18. An analytical reagent for use in the quantitative determination of at least one ketone body selected from the group consisting of D-3-hydroxybutyric acid and acetoacetic acid, which comprises:

(1) a D-3-hydroxybutyrate dehydrogenase as a first dehydrogenase which utilizes the following coenzymes (i) and (ii):
    (i) a first coenzyme selected from the group consisting of thionicotinamide adenine dinucleotide phosphate or its analog (thio-NADP compound) and thionicotinamide adenine dinucleotide or its analog (thio-NAD compound), and
    (ii) a second coenzyme selected from the group consisting of nicotinamide adenine dinucleotide phosphate or its analog (NADP compound) and nicotinamide adenine dinucleotide or its analog (NAD compound),
    and catalyzes the reversible reaction producing acetoacetic acid from D-3-hydroxybutyric acid as a substrate;

(2) at least one coenzyme selected from $A_1$ and $A_2$; and (3) $B_1$;

(5) a third dehydrogenase which does not react with D-3-hydroxybutyric acid but acts to promote the reaction for converting $A_2$ to $A_1$, in combination with a substrate for said third dehydrogenase, wherein $A_1$ is a thio-NADP compound, a thio-NAD compound, an NADP compound or an NAD compound; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; $A_2$ is a reduced form of $A_1$.

19. A method for the quantitative determination of D-3-hydroxybutyric acid, which consists essentially of:

treating a biological sample containing D-3-hydroxybutyric acid and acetoacetic acid with acetoacetate decarboxylase to eliminate the acetoacetic acid;

reacting the resultant biological sample with a reagent comprising:

(1) a D-3-hydroxybutyrate dehydrogenase which utilizes the following coenzymes (i) and (ii):

(i) a first coenzyme selected from the group consisting of thionicotinamide adenine dinucleotide phosphate or its analog (thio-NADP compound) and thionicotinamide adenine dinucleotide or its analog (thio-NAD compound), and (ii) a second coenzyme selected from the group consisting of nicotinamide adenine dinucleotide phosphate or its analog (NADP compound) and nicotinamide adenine dinucleotide or its analog (NAD compound), and catalyzes the reversible reaction producing acetoacetic acid from D-3-hydroxybutyric acid as a substrate;

(2) $A_1$; and (3) $B_1$;

said components (1), (2) and (3) participating in the following cycling reaction:

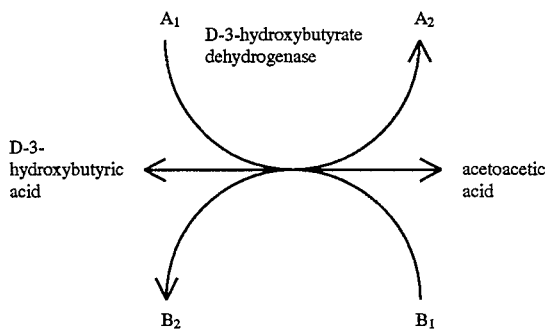

wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized form of $B_1$, wherein the reaction of said biological sample with said reagent is conducted under conditions adapted for the enzymatically catalytic and cycling reaction, thereby effecting the cycling reaction; and measuring and correlating a change in the amount of $A_2$ or $B_1$ to the quantity of said D-3 hydroxybutyric acid.

20. A method for the quantitative determination of at least one ketone body selected from the group consisting of D-3-hydroxybutyric acid and acetoacetic acid, which comprises:

reacting a biological sample containing at least one ketone body selected from the group consisting of D-3-hydroxybutyric acid and acetoacetic acid with a reagent comprising:

(1) a D-3-hydroxybutyrate dehydrogenase which utilizes the following coenzymes (i) and (ii):

(i) a first coenzyme selected from the group consisting of thionicotinamide adenine dinucleotide phosphate or its analog (thio-NADP compound) and thionicotinamide adenine dinucleotide or its analog (thio-NAD compound), and (ii) a second coenzyme selected from the group consisting of nicotinamide adenine dinucleotide phosphate or its analog (NADP compound) and nicotinamide adenine dinucleotide or its analog (NAD compound), and catalyzes the reversible reaction producing acetoacetic acid from D-3-hydroxybutyric acid as a substrate;

(2) $A_1$; and (3) $B_1$;

said components (1), (2) and (3) participating in the following cycling reaction:

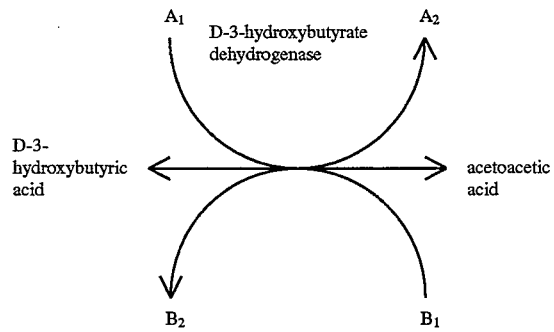

wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized form of $B_1$, wherein the reaction of said biological sample with said reagent is conducted under conditions adapted for the enzymatically catalytic and cycling reaction, thereby effecting said cycling reaction; and measuring and correlating a change in the amount of $A_2$ or $B_1$ to the quantity of said at least one ketone body, wherein each of $A_1$ and $B_1$ is used in a concentration of 0.02 to 100 mM or more, and the D-3-hydroxybutyrate dehydrogenase is used in a concentration of 5 to 1,000 U/ml or more.

21. A method for the quantitative determination of at least one ketone body selected from the group consisting of D-3-hydroxybutyric acid and acetoacetic acid, which comprises:

reacting a biological sample containing at least one ketone body selected from the group consisting of D-3-hydroxybutyric acid and acetoacetic acid with a reagent comprising:

(1) a D-3-hydroxybutyrate dehydrogenase as a first dehydrogenase which utilizes the following coenzymes (i) and (ii):

(i) a first coenzyme selected from the group consisting of thionicotinamide adenine dinucleotide phosphate or its analog (thio-NADP compound) and thionicotinamide adenine dinucleotide or its analog (thio-NAD compound), and (ii) a second coenzyme selected from the group consisting of nicotinamide adenine dinucleotide phosphate or its analog (NADP compound) and nicotinamide adenine dinucleotide or its analog (NAD compound), and catalyzes the reversible reaction producing acetoacetic acid from D-3-hydroxybutyric acid as a substrate;

(2) $A_1$;
(3) at least one coenzyme selected from $B_1$ and $B_2$; and
(4) a second dehydrogenase which does not react with D-3-hydroxybutyric acid but acts to promote the reaction for converting $B_2$ to $B_1$ in the following cycling reaction, in combination with a substrate for said second dehydrogenase:

said components (1), (2), (3) and (4) participating in the following cycling reaction:

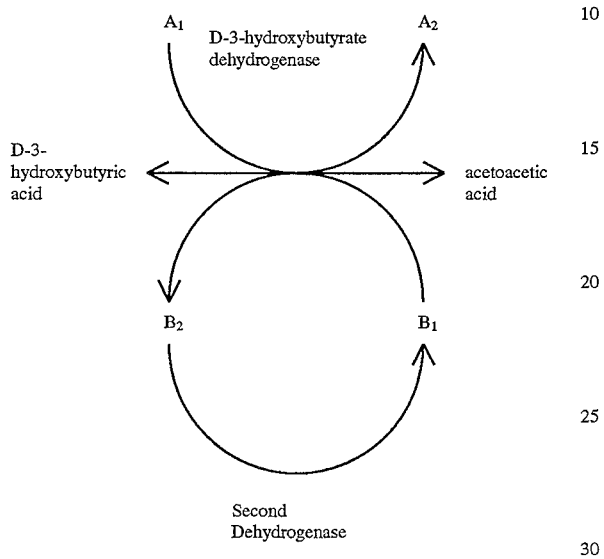

Second Dehydrogenase wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; $B_2$ is an oxidized form of $B_1$; and $B_1 \to B_1$ represents an enzymatic reaction producing $B_1$ from coenzyme $B_2$ under the action of said second dehydrogenase, wherein the reaction of said biological sample with said reagent is conducted under conditions adapted for the enzymatically catalytic and cycling reaction, thereby effecting the cycling reaction; and measuring and correlating a change in the amount of $A_2$ to the quantity of said at least one ketone body, wherein $A_1$ is used in a concentration of 0.02 to 100 mM or more, at least one coenzyme selected from $B_1$ and $B_2$ is used in a concentration of 0.05 to 5000 μM or more, said D-3-hydroxybutyrate dehydrogenase as the first dehydrogenase is used in a concentration of 5 to 1000 U/ml or more, the second dehydrogenase is used in a concentration which is 20 times or more the Km value thereof for $B_2$, and the substrate for the second dehydrogenase is used in a stoichiometrically excess amount.

22. A method for the quantitative determination of at least one ketone body selected from the group consisting of D-3-hydroxybutyric acid and acetoacetic acid, which comprises:

reacting a biological sample containing at least one ketone body selected from the group consisting of D-3-hydroxybutyric acid and acetoacetic acid with a reagent comprising:
(1) a D-3-hydroxybutyrate dehydrogenase as a first dehydrogenase which utilizes the following coenzymes (i) and (ii):

(i) a first coenzyme selected from the group consisting of thionicotinamide adenine dinucleotide phosphate or its analog (thio-NADP compound) and thionicotinamide adenine dinucleotide or its analog (thio-NAD compound), and
(ii) a second coenzyme selected from the group consisting of nicotinamide adenine dinucleotide phosphate or its analog (NADP compound) and, nicotinamide adenine dinucleotide or its analog (NAD compound), and catalyzes the reversible reaction producing acetoacetic acid from D-3-hydroxybutyric acid as a substrate;
(2) at least one coenzyme selected from $A_1$ and $A_2$;
(3) $B_1$; and
(5) a third dehydrogenase which does not react with D-3-hydroxybutyric acid but acts to promote the reaction for converting $A_2$ to $A_1$, in the following cycling reaction, in combination with a substrate for said third dehydrogenase:

said components (1), (2), (3) and (5) participating in the following cycling reaction:

Third Dehydrogenase

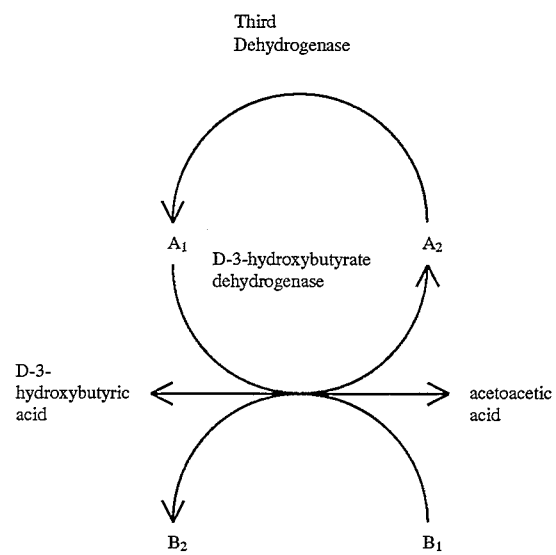

wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; $B_2$ is an oxidized form of $B_1$; and $A_2 \to A_1$ represents an enzymatic reaction producing $A_1$ from coenzyme $A_2$ under the action of said third dehydrogenase, wherein the reaction of said biological sample with said reagent is conducted under conditions adapted for the enzymatically catalytic and cycling reaction, thereby effecting the cycling reaction; and measuring and correlating a change in the amount of $B_1$ to the quantity of said at least one ketone body, wherein at least one coenzyme selected from $A_1$ and $A_2$ is used in a concentration of 0.05 to 5000 μM or more, $B_1$ is used in a concentration of 0.02 to 100 mM or more, said D-3-hydroxybutyrate dehydrogenase as the first dehydrogenase is used in a concentration of 5 to 1000 U/ml or more, the third dehydrogenase is used in a concentration which is 20 times or more the Km value thereof for $A_2$, and the substrate for the third dehydrogenase is used in a stoichiometrically excess amount.

23. An analytical reagent for use in the quantitative determination of at least one ketone body selected from the group consisting of D-3-hydroxybutyric acid and acetoacetic acid, which comprises:
1) a D-3-hydroxybutyrate dehydrogenase which utilizes the following coenzymes (i) and (ii):
   (i) a first coenzyme selected from the group consisting of thionicotinamide adenine dinucleotide phosphate or its analog (thio-NADP compound) and thionicotinamide adenine dinucleotide or its analog (thio-NAD compound), and
   (ii) a second coenzyme selected from the group consisting of nicotinamide adenine dinucleotide phosphate or its analog (NADP compound) and nicotinamide adenine dinucleotide or its analog (NAD compound),
   and catalyzes the reversible reaction producing acetoacetic acid from D-3-hydroxybutyric acid as a substrate;
(2) $A_1$; and
(3) $B_1$;
wherein $A_1$ is a thio-NADP compound, a thio-NAD compound, an NADP compound or an NAD compound; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound, and wherein each of $A_1$ and $B_1$ is present in a concentration of 0.02 to 100 mM or more, and the D-3-hydroxybutyrate dehydrogenase is present in a concentration of 5 to 1,000 U/ml or more.

24. An analytical reagent for use in the quantitative determination of at least one ketone body selected from the group consisting of D-3-hydroxybutyric acid and acetoacetic acid, which comprises:
(1) a D-3-hydroxybutyrate dehydrogenase as a first dehydrogenase which utilizes the following coenzymes (i) and (ii):
   (i) a first coenzyme selected from the group consisting of thionicotinamide adenine dinucleotide phosphate or its analog (thio-NADP compound) and thionicotinamide adenine dinucleotide or its analog (thio-NAD compound), and
   (ii) a second coenzyme selected from the group consisting of nicotinamide adenine dinucleotide phosphate or its analog (NADP compound) and nicotinamide adenine dinucleotide or its analog (NAD compound),
   and catalyzes the reversible reaction producing acetoacetic acid from D-3-hydroxybutyric acid as a substrate;
(2) $A_1$;
(3) at least one coenzyme selected from $B_1$ and $B_2$; and
(4) a second dehydrogenase which does not react with D-3-hydroxybutyric acid but acts to promote the reaction for converting $B_2$ to $B_1$, in combination with a substrate for said second dehydrogenase,
wherein $A_1$ is a thio-NADP compound, a thio-NAD compound, an NADP compound or an NAD compound; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; $B_2$ is an oxidized form of $B_1$, and wherein $A_1$ is present in a concentration of 0.02 to 100 mM or more, at least one coenzyme selected from $B_1$ and $B_2$ is present in a concentration of 0.05 to 5000 μM or more, said D-3-hydroxybutyrate dehydrogenase as the first dehydrogenase is present in a concentration of 5 to 1000 U/ml or more, the second dehydrogenase is present in a concentration which is 20 times or more the Km value thereof for $B_2$, and the substrate for the second dehydrogenase is present in a stoichiometrically excess amount.

25. An analytical reagent for use in the quantitative determination of at least one ketone body selected from the group consisting of D-3-hydroxybutyric acid and acetoacetic acid, which comprises:
(1) a D-3-hydroxybutyrate dehydrogenase as a first dehydrogenase which utilizes the following coenzymes (i) and (ii):
   (i) a first coenzyme selected from the group consisting of thionicotinamide adenine dinucleotide phosphate or its analog (thio-NADP compound) and thionicotinamide adenine dinucleotide or its analog (thio-NAD compound), and
   (ii) a second coenzyme selected from the group consisting of nicotinamide adenine dinucleotide phosphate or its analog (NADP compound) and nicotinamide adenine dinucleotide or its analog (NAD compound),
   and catalyzes the reversible reaction producing acetoacetic acid from D-3-hydroxybutyric acid as a substrate;
(2) at least one coenzyme selected from $A_1$ and $A_2$; and
(3) $B_1$;
(5) a third dehydrogenase which does not react with D-3-hydroxybutyric acid but acts to promote the reaction for converting $A_2$ to $A_1$, in combination with a substrate for said third dehydrogenase,
wherein $A_1$ is a thio-NADP compound, a thio-NAD compound, an NADP compound or an NAD compound; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; $A_2$ is a reduced form of $A_1$, and wherein at least one coenzyme selected from $A_1$ and $A_2$ is present in a concentration of 0.05 to 5000 μM or more, $B_1$ is present in a concentration of 0.02 to 100 mM or more, and said D-3-hydroxybutyrate dehydrogenase as the first dehydrogenase is present in a concentration of 5 to 1000 U/ml or more, the third dehydrogenase is present in a concentration which is 20 times or more the Km value thereof for $A_2$, and the substrate for the third dehydrogenase is present in a stoichiometrically excess amount.

26. A method for the quantitative determination of D-3-hydroxybutyric acid, which comprises:
treating a biological sample containing D-3-hydroxybutyric acid and acetoacetic acid with acetoacetate decarboxylase to eliminate the acetoacetic acid;
reacting the resultant biological sample with a reagent comprising:
(1) a D-3-hydroxybutyrate dehydrogenase which utilizes the following coenzymes (i) and (ii):
   (i) a first coenzyme selected from the group consisting of thionicotinamide adenine dinucleotide phosphate or its analog (thio-NADP compound) and thionicotinamide adenine dinucleotide or its analog (thio-NAD compound), and (ii) a second coenzyme selected from the group consisting of nicotinamide adenine dinucleotide phosphate or its analog (NADP compound) and nicotinamide adenine dinucleotide or its analog (NAD compound), and catalyzes the reversible reaction producing acetoacetic acid from D-3-hydroxybutyric acid as a substrate;

(2) $A_1$; and (3) $B_1$; said components (1), (2) and (3) participating in the following cycling reaction:

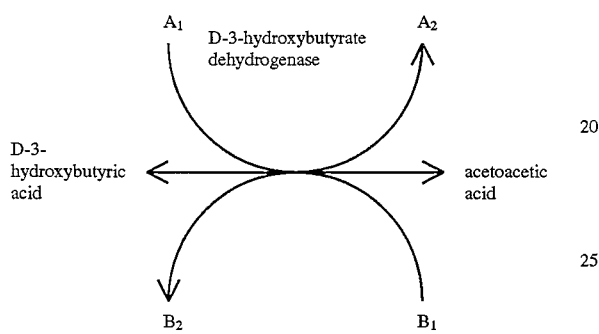

wherein $A_1$ is a thio-NADP compound, a thio-NAD compound, an NADP compound or an NAD compound; $A_2$ is a reduced form of $A_1$; $B_1$ is a reduced NADP compound or a reduced NAD compound when $A_1$ is a thio-NADP compound or a thio-NAD compound, or a reduced thio-NADP compound or a reduced thio-NAD compound when $A_1$ is an NADP compound or an NAD compound; and $B_2$ is an oxidized form of $B_1$, wherein the reaction of said biological sample with said reagent is conducted under conditions adapted for the enzymatically catalytic and cycling reaction, thereby effecting the cycling reaction; and measuring and correlating a change in the amount of $A_2$ or $B_1$ to the quantity of said D-3-hydroxybutyric acid, wherein each of $A_1$ and $B_1$ is used in a concentration of 0.02 to 100 mM or more, and the D-3-hydroxybutyrate dehydrogenase is used in a concentration of 5 to 1,000 U/ml or more.

* * * * *